United States Patent [19]

Imre et al.

[11] Patent Number: 5,710,342
[45] Date of Patent: Jan. 20, 1998

[54] PROCESS FOR PREPARING CARBONYL COMPOUNDS BY CATALYSED OXIDATION OF OLEFINS AND CATALYSTS PRESENT MICROEMULSIONS

[75] Inventors: Laszlo Imre; Reinhard Schomäcker; Judit Daun, all of Leverkusen, Germany

[73] Assignee: Bayer Aktiengesellschaft, Leverkusen, Germany

[21] Appl. No.: 568,054

[22] Filed: Dec. 6, 1995

[30] Foreign Application Priority Data

Dec. 15, 1994 [DE] Germany ............ 44 44 738.8

[51] Int. Cl.$^6$ .................................... C07C 45/34
[52] U.S. Cl. ................ 568/360; 568/401; 568/475
[58] Field of Search ..................... 568/360, 401, 568/475

[56] References Cited

U.S. PATENT DOCUMENTS

| | | | |
|---|---|---|---|
| 4,152,354 | 5/1979 | Stopp | 568/360 |
| 4,271,320 | 6/1981 | Tohitoh et al. | 568/360 |
| 4,568,770 | 2/1986 | Alper et al. | 568/360 |
| 4,806,692 | 2/1989 | Yamada et al. | 568/360 |
| 5,237,103 | 8/1993 | Saito et al. | 568/360 |
| 5,414,137 | 5/1995 | Ishii et al. | 568/360 |

FOREIGN PATENT DOCUMENTS

| | | | |
|---|---|---|---|
| 0000143 | 1/1979 | European Pat. Off. | 568/475 |
| 2612512 | 9/1988 | France | 568/475 |
| 1049845 | 2/1959 | Germany | 568/360 |
| 1061767 | 7/1959 | Germany | 568/401 |
| 1080994 | 5/1960 | Germany | 568/360 |
| 2618055 | 11/1977 | Germany | 568/360 |
| 2805402 | 8/1979 | Germany | 568/360 |
| 3305000 | 10/1983 | Germany | 568/360 |
| 1516617 | 7/1978 | United Kingdom | 568/401 |

OTHER PUBLICATIONS

Chemical Abstracts, vol. 100, Abstract of JP 58-144,354, p. 565 (1984).
Chemical Abstracts, vol. 55, Abstract No. 3436d, Abstract of German 1,049,845 (1959).
Chemical Abstracts, vol. 91, Abstracts No. 175011k, Abstract of DE 28 50 330, (1979).
Chemical Abstracts, vol. 55, Abstract No. 18596f, Abstract of German 1,080,994 (1960).
Chemical Abstracts, vol. 55, Abstract No.11304b, Abstract of German 1,061,767 (1959).
N. Alandis, et al., Bull. Soc. Chim. Fr., No. 2, pp. 252-(1989).

*Primary Examiner*—James H. Reamer
*Attorney, Agent, or Firm*—Sprung Kramer Schaefer & Briscoe

[57] ABSTRACT

Carbonyl compounds can be prepared by catalytic oxidation of olefins with oxygen or oxygen-containing gases in a microemulsion (ME) as reaction medium and catalyst support. The catalysts present in ME and used for this purpose are characterized by a content of 0.0001–10% by weight of a Pd compound and by a content of 0.0005–20% by weight of a subgroup metal compound or a quinone, based on the total weight of the catalysts present in the ME.

14 Claims, No Drawings

PROCESS FOR PREPARING CARBONYL COMPOUNDS BY CATALYSED OXIDATION OF OLEFINS AND CATALYSTS PRESENT MICROEMULSIONS

BACKGROUND OF THE INVENTION

The present invention relates to the oxidation of open-chain or cyclic olefins in a microemulsion as reaction medium and catalyst support with formation of compounds containing a carbonyl function (open-chain or cyclic aldehydes and ketones), and also the catalysts present in microemulsions.

A known and generally usable process is the oxidation of C—C double bonds using ozone as oxidate (Houben-Weyl: Methoden der Organischen Chemie [Methods of Organic Chemistry], Stuttgart 1952, Volume 7/1, Page 333 f). This process has often been employed for the solution of chemical problems in the laboratory, but has not been able to achieve any industrial importance since the preparation and handling of ozone is very complicated and the handling of the highly explosive ozonides obtained as intermediates entails considerable risks.

Further oxidants which have been described for the reaction of C—C double bonds are, for example, potassium permanganate, chromic acid, nitric acid, osmium tetroxide, hydrogen peroxide/osmium tetraoxide, lead tetraacetate and periodic acid, which have been used specifically for the solution of individual problems (Houben-Weyl: Methoden der Organischen Chemie [Methods of Organic Chemistry], Stuttgart 1952, Volume 7/1, Pages 347, 351 f).

All these methods are very complicated, require expensive oxidants and are linked to specific structural prerequisites.

For the oxidation of olefins on an industrial scale, both in the gas phase and in the liquid phase, a number of catalytic processes have become known from the patent literature.

In carrying out oxidations of olefins in the gas phase in the presence of solid catalysts, the selectivities achieved are generally unsatisfactory. Such processes therefore do not come into question for many compounds (U.S. Pat. No. 3,946,081 (1976); Ullmann's Encyklopädie der technischen Chemie [Ullmann's Encyclopedia of Industrial Chemistry], 4th Edition, Volume 17, Page 483 f).

In carrying out oxidation reactions in the liquid phase, the introduction of the catalyst (usually inorganic compounds) into the reaction mixture generally presents a serious problem owing to the low solubility of inorganic compounds in the organic compounds. Owing to the low catalyst concentration associated therewith, the reactions are carried out at relatively high temperatures and therefore only low conversions and unsatisfactory selectivities are often obtained (DE-OS (German Published Specification) 2 618 055; DE-OS (German Published Specification) 2 805 402).

In the Wacker-Hoechst process, ethylene is oxidized on an industrial scale with oxygen or air in an aqueous phase in the presence of palladium chloride and copper chloride at 90°–130° C. and a pressure of up to 10 bar to give acetaldehyde (German Patent Specification 1 049 845, 1 061 767, 1 080 994; see also Winnacker-Küchler, Chemische Technologie [Chemical Technology], Volume 6, 4th Edition, Page 66 f (1982)). The process is carried out in either one or two stages (in the two-stage process, the reoxidation of the catalyst solution is carried out in a separate stage). It is an elegantal process used worldwide, but it is fundamentally desirable to be able to work at significantly lower temperatures.

Furthermore, DE-OS (German Published Specification) 3 305 000 describes the oxidation of cyclopentene to cyclopentanone in the presence of Wacker-Hoechst catalysts in alcoholic solutions. However, the solubility of the catalyst salts, which are fed in the solid state into the reaction vessel, is very low in organic alcoholic systems, their concentration is therefore undefined.

SUMMARY OF THE INVENTION

In contrast, it has now been found that the oxidation of olefins to form carbonyl compounds (open-chain or cyclic aldehydes and ketones) can be carried out with high selectivity by reacting the olefins with oxygen or oxygen-containing gases at low temperatures in the presence of catalysts in microemulsions as reaction media.

The invention provides a process for preparing carbonyl compounds of the formula

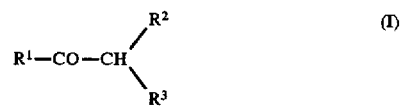

by catalytic oxidation of olefins of the formula

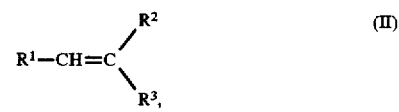

where, in the formulae $R^1$, $R^2$ and $R^3$ are, independently of one another, hydrogen; straight-chain or branched $C_1$–$C_8$-alkyl which is unsubstituted or monosubstituted or disubstituted by halogen, hydroxy, cyano, COO—$C_1$–$C_4$-alkyl, CO—$C_1$–$C_4$-alkyl, $SO_2$—O—$C_1$–$C_2$-alkyl or phenyl; or phenyl or naphthyl which are unsubstituted or monosubstituted or disubstituted by halogen, hydroxy, nitro, cyano, $C_1$–$C_4$-alkyl, COO—$C_1$–$C_4$-alkyl, CO—$C_1$–$C_4$-alkyl or $SO_2$—O—$C_1$–$C_4$-alkyl, and $R^1$ and $R^3$ or $R^2$ and $R^3$ can furthermore together form an alkylene chain –(CH$_2$)$_m$– where m=3–10 and 1–2 of the alkylene chain C-atoms can be substituted by halogen, hydroxy, $C_1$–$C_4$-alkyl, COO—$C_1$–$C_4$-alkyl, CO—$C_1$–$C_4$-alkyl, $SO_2$—O—$C_1$–$C_4$-alkyl or phenyl, by oxygen or oxygen-containing gases, which is characterized in that the oxidation is carried out at 0°–200° C. and 0.2–200 bar in the presence of a catalyst system comprising a palladium compound and one or more reoxidizing agents from the group of compounds of further subgroup metals and quinones, in a microemulsion as reaction medium and catalyst support.

DETAILED DESCRIPTION OF THE INVENTION

The olefins to be reacted according to the invention can be introduced into reaction media comprising organic components, water and surfactants to form a single-phase system (microemulsion ME). Single-phase ME can also take up as catalysts the inorganic salts otherwise not soluble in organic systems. The ME is thus simultaneously reaction medium and catalyst support.

The invention accordingly further provides catalysts present in ME, in particular catalysts for reactions in which both starting materials and products are gaseous. After the reaction is complete, the products and any starting materials which have not completely reacted leave the catalyst present in the ME, so that the catalyst is available for further reactions. This is formally analogous to heterogeneous solid catalysts; in contrast to these the contact between the catalysts present in ME and starting materials is much more intensive as a result of the "solubility of the starting materials in the catalysts".

Oxidations in single-phase systems have advantages over oxidations in two-phase or multiphase systems. The ME forms spontaneously even under gentle stirring from a mixture of water, organic compounds, for example the olefin to be reacted and optionally further organic solvents, and the surfactant. The dispersion formed is optically transparent and thermodynamically stable, i.e. even after long periods there is no separation of the ME into two phases (Angewandte Chemie 97, (1985), 655; Ullmann, Vol. 9, Page 310; Römpp, Chemie Lexikon [Encyclopedia of Chemistry], p. 2779). The droplet size of the ME is established as a function of the composition in the range from 5 to 100 nm and is independent of the power input by means of which dispersion is carried out. Since the droplet size is far below the wavelength of visible light, the ME is optically transparent like a true solution, although droplets are present as in an emulsion. The difference from a normal emulsion is, on the one hand, in the size of the droplets (ME: from 5 to 100 nm; other emulsions: from 0.5 to 10 µm) and, on the other hand, in the thermodynamic stability of the ME. While an appreciable amount of mechanical energy has to be used for preparing a normal emulsion, a ME spontaneously forms from the components with gentle stirring. This preparative process for the ME is comparable with the mixing of two miscible liquids.

It has been found that for the formation of the ME required according to the invention it is important that the composition and the temperature of the mixture is within the single-phase region of the phase diagram of the system in question. Each ternary mixture of water, olefin (and optionally additional organic solvent) and a surfactant has its own phase diagram. In these various phase diagrams, the single-phase region is in each case found at different temperatures and compositions. The temperature range of the single-phase region is determined by the hydrophilicity of the surfactant, i.e. is shifted to higher temperatures with increasing hydrophilicity. The use of surfactant mixtures enables the temperature range of the single-phase region to be adjusted specifically to a desired temperature.

For the reaction mixtures, the surfactant (or surfactant mixture) is selected so that the single-phase region extends over the desired compositions and the desired temperature range (e.g. room temperature). Adjacent to the single-phase region are two-phase regions in which normal, unstable emulsions occur.

Ionic and nonionic surfactants are suitable for preparing the ME. A single surfactant or a mixture of a plurality of surfactants, preferably from 1 to 3 can be used.

Specific examples which may be mentioned are: n-($C_8$–$C_{18}$)-alkyl-sulphonates, n-($C_8$–$C_{18}$)-alkyl-benzene-sulphonates, n-($C_8$–$C_{18}$)-alkyl-trimethyl-ammonium salts, di(n-($C_8$–$C_{18}$)-alkyl)dimethyl-ammonium salts, n-($C_8$–$C_{18}$)-alkyl-carboxylates, oligoethylene oxide-$EO_{2\text{-}30}$-mono-n-($C_6$–$C_{18}$)-alkyl ethers, n-($C_8$–$C_{18}$)-alkyl-dimethylamine oxide, n-($C_8$–$C_{18}$)-alkyldimethylphosphine oxide or oligoethylene oxide monoaryl ethers. The n-alkyl chains can also be replaced by partially unsaturated chains.

The ME comprises (i) from 1 to 20% by weight of water, (ii) from 60 to 97% by weight of one or more inorganic components from the group of olefins to be reacted and organic solvents and (iii) from 2 to 20% by weight of one or more surfactants, all based on the total weight of the ME.

Suitable catalysts for the process of the invention are a palladium compound and, as cocatalyst, at least one reoxidizing agent from the group of compounds of the transition metals of the first, second and third transition series, and also the actinides, as are described in DE-OS (German Published Specification) 26 18 055 and Hollemann-Wiberg, Lehrbuch der anorganischen Chemie [Textbook of Inorganic Chemistry], 1971, Pages 672 to 680, and of quinones. The reoxidizing agents effect a reoxidation of the Pd catalyst which has itself been reduced by the oxidation of the olefin; the reoxidizing agent reduced in this way is then reconverted into the oxidized state by means of oxygen. The quinones can also be used in the form of the corresponding hydroquinones. Suitable quinones are o- and p-benzoquinone, naphthoquinone, anthraquinone and others known to those skilled in the art; they can be substituted by from 1 to 4 halogen atoms (F, Cl, Br), $C_1$–$C_4$-alkyl groups or $C_1$–$C_4$-alkoxy groups, including different ones of these. Preferably, transition metal compounds which occur in various oxidation states as reoxidizing agent. The reoxidizing agents are hereinafter referred to as cocatalyst.

Preference is given to using compounds of the following elements in combination with Pd as catalyst: iron, cobalt, nickel, copper, chromium, tin, antimony, cerium, rhodium, platinum, gold.

Suitable compounds of the abovementioned transition elements are (DE-OS (German Published Specification) 2 618 055):

salts of inorganic adds,
salts of organic carboxylic acids,
complex salts of the elements,
alkoxides of aliphatic, cycloaliphatic, araliphatic and aromatic alcohols.

Of course, it is also possible to use mixtures of the various abovementioned cocatalysts.

In place of the compounds of the transition elements as cocatalyst, it is also possible to use organic compounds such as, for example, quinones.

The process of the invention is preferably carried out in the presence of a catalyst system comprising palladium chloride or palladium nitrate and iron nitrate.

The concentration of the salts in the catalyst system in the ME can be varied within wide limits. The amount of palladium compound added can be, for example, from 0.0005 to 10% by weight, preferably from 0.05 to 1% by weight, of the ME. The concentration of the cocatalyst can be below or above the concentration of the palladium compound, for example 0.0001–20% by weight of the ME. Advantageously, the concentration of the cocatalyst is set higher than that of the palladium compound, preferably by a factor of from 2 to 100.

The catalyst is introduced into a ME by starting with an aqueous solution which forms a single-phase solution with the ME. The catalyst can also be dissolved directly in the ME.

Suitable olefins for the process of the invention are, for example, those of the above formula (II) with the scope of definitions specified.

Preferred olefins are those of the formula

where
R$^{11}$ and R$^{12}$ are, independently of one another, hydrogen; straight-chain or branched C$_1$–C$_4$-alkyl which is unsubstituted or substituted by halogen, hydroxy, COO—CH$_3$, CO—CH$_3$ or phenyl; or phenyl which is unsubstituted or substituted by halogen, hydroxy, nitro, CH$_3$, C$_2$H$_5$, COO—CH$_3$ or CO—CH$_3$, and
R$^{13}$ is hydrogen or methyl; and
R$^{11}$ and R$^{13}$ or R$^{12}$ and R$^{13}$ can together form trimethylene, tetramethylene or pentamethylene.

The organic part of the ME can be made up only of the olefin to be reacted. However, it is also possible to use, in addition, an oxidation-resistant organic water-immiscible solvent in an amount of 10–1000% by weight of the amount of the olefin to be reacted. Such solvents are, for example: C$_4$–C$_{20}$-alkanes or C$_6$–C$_{10}$-aromatics, which can also be substituted by halogen, nitro or ester groups and are well known to those skilled in the art as typical organic solvents.

In general, in the process of the invention, temperature and pressure can be varied within wide limits.

Thus, the process of the invention can be carried out in a temperature range between 0° and 200° C. It is advantageously carried out in the temperature range from about 10° to 80° C., in particular at 15°–40° C. (vicinity of room temperature). Carrying out the reaction in the vicinity of room temperature is termed cold oxidation.

The reaction can be carried out at atmospheric pressure, reduced or increased pressure; in general, the pressure range between 0.2 and 200 bar is suitable. The reaction is advantageously carried out in the pressure range from 0.5 to 100 bar, in particular from 1 to 10 bar.

The oxidant used in the process of the invention can be pure oxygen. It can also be used as a mixture with one or more inert gases such as nitrogen, argon, carbon dioxide, of course also in the form of air.

The reaction time in the process of the invention can be varied within wide limits. It can be, for example, from 0.1 to 20 hours, preferably from 0.25 to 10 hours, and depends, inter alia, on the batch size.

To carry out the process of the invention, the ME can be formed together with the olefin to be oxidized, for example with cyclopentene or cyclohexene, and the desired catalyst is then introduced into the microemulsion. The entire system here remains as a single phase. This system is then brought into intimate contact with oxygen or an oxygen-containing gas mixture by means of fine distribution. The process of the invention can here be carried out batchwise in the simplest manner in a stirred autoclave under an appropriate oxygen pressure and suitable temperature, with the oxygen pressure having to be at least high enough for the amount of oxygen to be sufficient for achieving the desired conversion. However, it is generally more advantageous, even when carrying out the process of the invention in an intrinsically batchwise manner, to pass oxygen continuously into the liquid phase and to maintain the gas stream at constant pressure and constant flow rate by means of a valve system for gas supply and gas discharge (DE-OS (German Published Specification) 26 18 055).

To achieve a high selectivity for the desired reaction product, it can be advantageous to carry out the reaction in such a way that only a partial conversion is achieved; this can be achieved in a known manner, for example, by appropriate selection of the reaction conditions, pressure and temperature, but also of the composition of the liquid phase or gas phase, and the type and amount of catalyst.

After reaching the desired conversion, the reaction mixture is worked up. This can be carried out, for example, by distillation.

The great advantage of the procedure according to the invention of working in ME is that the work-up of the reaction mixture for isolating the product can be carried out significantly more simply as a result of the chemical and physical properties of ME. The work-up is preferably carded out as follows: lowering the temperature compared with the reaction temperature causes the ME to separate into a first phase containing the predominant part of the surfactant and of the water (including the catalyst) and into a second phase in which the product and unreacted olefin (possibly together with an additional solvent) are present. The latter phase is worked up by distillation. The catalyst-containing phase can be admixed with fresh starting material and recirculated to the reaction. The phase separation can be caused in part just by the formation of the reaction production at reaction temperature. Depending on the type of olefin reacted, the product has a different degree of influence on the stability of the ME, so that temperature changes of different sizes are necessary for the separation of the ME into the two phases. Such a separation can also be carried out continuously.

If the olefins to be reacted and products are gaseous at reaction temperature, the process of the invention is, in a preferred embodiment, carried out as follows: the prepared ME containing the catalyst is first placed without the olefin to be reacted in a suitable reaction vessel, for example in an autoclave. The gas mixture containing both the olefin to be reacted and also the oxidant, for example the oxygen, is then continuously passed into, and mixed with, this ME. The gas stream can here be maintained at constant pressure with constant flow rate by means of a valve system for gas supply and gas discharge. The flow rate of the gas mixture enables any desired reaction time ("contact time") corresponding to the desired conversion to be set. The gas mixture flowing out contains the reaction product which is conducted away for work-up. The work-up is thus restricted only to the gas mixture leaving the reactor, which can be carried out in a known manner. According to this variant of the process of the invention, the ME is used as catalyst support, similar to a solid catalyst support material, continuously over a relatively long period of time.

The process of the invention has the advantage compared with the prior art that olefins can, in a simple manner, be oxidized continuously or batchwise at a high selectivity.

Compounds which can be prepared by the process of the invention, namely open-chain or cyclic aldehydes and ketones, are used, as is known, in many organic syntheses as intermediates.

EXAMPLES

Apparatus

In the following examples, use was made of a commercial autoclave of stainless steel (from Carl Roth) having a volume of 200 ml. The autoclave was designed for a working pressure of up to 100 bar and a working temperature of up to 300° C. The desired operating temperature was set by means of a heating mantle kept constant by means of an electrical regulator. The gases (air, oxygen) were taken from a steel bottle via a pressure valve. For this purpose, Teflon pipes sheathed with steel fabric were used. The desired working pressure was set by means of valves of a pressure gauge. So as not to exceed the operating pressure of 100 bar, a safety valve set to 95 bar was additionally installed between the autoclave and the steel bottle. The reaction solution was placed in the autoclave in a glass beaker having a volume of 40 ml and was stirred from the outside using a magnetic stirrer. The rotation speed of the stirrer allowed a fine distribution of the gas in the reaction solution. The cleaning of the autoclave was carried out in the cold state using ethanol. The autoclave and the venting valve were blown out with dry and pure nitrogen before each experiment. Furthermore, glass vessels were cleaned in an ultrasonic bath. After closing the autoclave, it was pressurised to the desired working pressure with the oxidizing gas (air or oxygen) from a steel bottle. The inlet valve was then closed so that further feed of gas was no longer possible. The magnetic stirrer was then turned on and the contents of the autoclave were heated to the desired temperature. After the reaction time had expired, the autoclave was taken from the heating mantle and cooled in ice water. After cooling, the glass vessel together with its contents was then removed and analyzed.

Reaction media

The reaction media used were microemulsions (ME) which were formed together with the compounds to be oxidized (cyclopentene or cyclohexene) and catalysts. The compositions of these ME are shown in Table 1.

TABLE 1

Microemulsions (ME), Total 100% by weight without catalyst

| Composition [% by weight] | ME1 | ME2 | ME3 | ME4 | ME5 | ME6 | ME7 |
|---|---|---|---|---|---|---|---|
| Cyclopentene | 39.3 | 32.1 | 32.1 | 30.6 | — | — | — |
| Cyclohexene | — | — | — | — | 30.2 | 30.2 | 30.2 |
| n-Heptane | 39.3 | 32.1 | 32.1 | 30.6 | — | — | — |
| n-Octane | — | — | — | — | 30.2 | 30.2 | 30.2 |
| Igepal* | 10.1 | 8.3 | 8.3 | 11.8 | — | — | — |
| Triton** | 3.5 | 6.7 | 6.7 | 5.8 | 18.8 | 18.8 | 18.8 |
| n-Propanol | — | 14.4 | 14.4 | 14.2 | 14.8 | 14.8 | 14.8 |
| Water | 7.8 | 6.4 | — | 7 | 6 | — | — |
| 1N Hydrochloric acid | — | — | 6.4 | — | — | 6 | — |
| 0.5N Sodium acetate | — | — | — | — | — | — | 6 |

TABLE 1-continued

Microemulsions (ME), Total 100% by weight without catalyst

Composition [% by weight]  ME1  ME2  ME3  ME4  ME5  ME6  ME7

*Igepal CA 520: 4-($C_8H_{17}$)$C_6H_4$O($CH_2CH_2$O)$_4$$CH_2CH_2$OH (from Aldrich)
**Triton X 100: 4-($C_8H_{17}$)$C_6H_4$O($CH_2CH_2$O)$_9$$CH_2CH_2$OH (from Aldrich)

Analysis

In carrying out the following examples, the identity of the compounds obtained was confirmed by gas-chromatographic and mass-spectroscopic analysis in comparison with authentic samples. Use was made of a gas chromatograph HP 5890 Series II fitted with a flame ionisation detector and automatic sample injection device. Separation columns used were capillary columns OV 1701. The length and the internal diameter of the columns were 25/50 m and 0.32 mm respectively. The injection block and the detector were set to 300° C. The temperature of the column was increased from 50° C. to 250° C. at a heating rate of 10° C./min. The carrier gas used was helium. The flow rate of the helium was 1.5 ml/min. The quantitative determination was carried out by the internal standard method. The standard used was n-nonane or n-decane. The substances were identified by means of a mass-selective detector.

Examples 1 to 19

A batch of 17 g (about 20 ml) containing the catalyst indicated in Tables 2 and 3 below was in each case introduced, in a 40 ml glass vessel, into the stirred autoclave described above and was oxidized at the temperatures and oxygen pressures indicated in these tables for the indicated time. Subsequently, the reaction product was analysed by gas chromatography and mass spectroscopy and also, as described further above, pure product was separated from the ME. The conversions and selectivities calculated from the gas-chromatographic analysis are likewise given in Tables 2 and 3.

TABLE 2

Examples 1 to 11: Oxidation of cyclopentene; % by weight of catalyst, based on the total batch

| Example | Micro-emulsion | Catalyst composition [% by weight] | T [°C.] | $pO_2$ [bar] | t [h] | Conversion of cyclo-pentene [%] | Selectivité [%] base on cyclopentanone |
|---|---|---|---|---|---|---|---|
| 1 | ME 1 | $PdCl_2$/$CuCl_2$: 0.8/6 | 46 | 18. Air | 4 | 10.4 | 72 |
| 2 | ME 2 | $PdCl_2$/$CuCl_2$: 0.7/4.9 | 46 | 18. Air | 4 | 20 | 85 |
| 3 | ME 3 | $PdCl_2$/$CuCl_2$: 0.7/4.9 | 46 | 18. Air | 4 | 37 | 83 |
| 4 | ME 3 | $PdCl_2$/$CuCl_2$: 0.05/4.9 | 48 | 18. Air | 4 | 18 | 84 |
| 5* | ME 4 | $PdCl_2$/$FeCl_3$: 0.7/2 | 48 | 18. Air | 4 | 61 | 83 |
| 6 | ME 4 | $PdCl_2$/$FeCl_3$: 0.7/2 | 15 | 1 | 6 | 3,5 | 90 |
| 7 | ME 4 | $PdCl_2$/$Fe(NO_3)_3$: 0.7/0.7 | 15 | 1 | 6 | 12 | 83 |
| 8 | ME 4 | $PdCl_2$/$Fe(NO_3)_3$: 0.7/1.4 | 15 | 1 | 6 | 28 | 85 |
| 9 | ME 4 | $PdCl_2$/$Fe(NO_3)_3$: 0.7/0.35 | 15 | 1 | 6 | 7 | 76 |
| 10 | ME 4 | $PdCl_2$/$Fe(NO_3)_3$: 0.1/0.35 | 15 | 1 | 6 | 6 | 82 |
| 11 | ME 4 | $PdCl_2$/$Fe(NO_3)_3$: 0.7/1.4 | 20 | 5 | 0.5 | 14 | 88 |

5*: Work-up gave 2.14 g of pure cyclopentanone

TABLE 3

Examples 12 to 19: Oxidation of cyclohexene, catalyst as in Table 2

| Example | Micro-emulsion | Catalyst composition [% by weight] | T [°C.] | $P_{O_2}$ [bar] | t [h] | Conversion of cyclo-hexene [%] | Selectivity [%] based on cyclo-hexanone |
|---|---|---|---|---|---|---|---|
| 12 | ME 5 | $PdCl_2/CuCl_2$: 0.7/4.9 | 68 | 18. Air | 4 | 12 | 64 |
| 13 | ME 5 | $PdBr_2/CuCl_2$: 0.7/4.9 | 73 | 18. Air | 4 | 30 | 30 |
| 14 | ME 5 | $PdCl_2/FeCl_3$: 0.7/2 | 30 | 1 | 6 | 3 | 80 |
| 15 | ME 5 | $PdCl_2/Fe(NO_3)_3$: 0.7/1.4 | 30 | 1 | 6 | 18 | 62 |
| 16 | ME 5 | $PdCl_2/(NH_4)_2Ce(NO_3)_6$: 0.5/0.8 | 30 | 1 | 6 | 8 | 68 |
| 17 | ME 5 | $PdCl_2/Fe(NO_3)_3/Ce(SO_4)_2$: 0.7/1.4/1.4 | 30 | 1 | 6 | 21 | 71 |
| 18 | ME 6 | $PdCl_2/Fe(NO_3)_3$: 0.7/1.4 | 30 | 1 | 6 | 9 | 68 |
| 19 | ME 7 | $PdCl_2/FeCl_3$: 0.7/2 | 30 | 1 | 6 | 1.5 | 77 |

Example 20: Oxidation of 1-octane

The autoclave described above was charged with 17 g of ME containing 1-octene as compound to be oxidized and having the following composition (in % by weight including catalyst): 54% of 1-octene, 7.7% of Igepal, 1.9% of Triton 100, 19.2% of n-propanol, 10.7% of water and 0.8% of $PdCl_2/5.7\%$ of $Fe(NO_3)_3$ as catalyst. The oxidation was carried out for 6 hours at 50° C. and 1 bar using pure oxygen. Methyl hexyl ketone was obtained as product. The selectivity was 54% at a conversion of 14%.

Example 21: Oxidation of ethene

For the oxidation of ethene, the above-described apparatus was used, but a gas stream was maintained through the autoclave at constant pressure with constant flow rate by means of a valve system (gas supply and gas discharge). To carry out the oxidation, the autoclave was charged with 50 g of ME comprising 39.37 g of n-heptane, 4.5 g of Igepal, 5 g of water, 1 g of 40% strength aqueous $Fe(NO_3)_3$ solution and 0.13 g of $PdCl_2$, and a gas mixture comprising 85% by volume of ethene and 15% by volume of oxygen was passed through the ME at 12 bar and 24° C. The flow rate was 0.8 l/h. The ME here served as catalyst support. In the exiting gas mixture, acetaldehyde and ethylene oxide were found as products by gas chromatography. In the steady state, the conversion was 1.4% of the ethene and the selectivity (based on acetaldehyde) was 62%.

Example 22: Oxidation of ethene

This was carried out as described in Example 21, but the gas stream was set to 98% by volume of oxygen and 2% by volume of ethene. This gave a conversion of 14% of the ethene. The selectivity, based on acetaldehyde, was 54%.

Example 23: Oxidation of propene

This was carried out as described in Example 21, but the gas stream was set to 42% by volume of oxygen and 48% by volume of propene and this was passed through the ME at a volumetric flow rate of 0.8 l/h at 2 bar total pressure and room temperature. The selectivity for the product acetone was 64%; propylene oxide was found as further product. The conversion was 0.9% of the propene.

What is claimed is:

1. A process for preparing a carbonyl compound of the formula

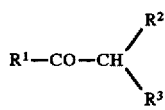

by catalytic oxidation of an olefin of the formula

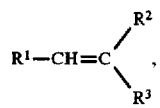

where, in the formulae $R^1$, $R^2$ and $R^3$ are, independently of one another, hydrogen; straight-chain or branched $C_1$–$C_8$-alkyl which is unsubstituted or monosubstituted or disubstituted by halogen, hydroxy, cyano, COO—$C_1$–$C_4$-alkyl, CO—$C_1$–$C_4$-alkyl, $SO_2$—O—$C_1$–$C_2$-alkyl or phenyl; or phenyl or naphthyl which are unsubstituted or mono-substituted or disubstituted by halogen, hydroxy, nitro, cyano, $C_1$–$C_4$-alkyl, COO—$C_1$–$C_4$-alkyl, CO—$C_1$–$C_4$-alkyl or $SO_2$—O—$C_1$–$C_4$-alkyl, and $R^1$ and $R^3$ or $R^2$ and $R^3$ can further more together form an alkylene chain –(CH$_2$)$_m$– where m=3–10 and 1–2 of the alkylene chain carbon atoms can be substituted by halogen, hydroxy, $C_1$–$C_4$-alkyl, COO—$C_1$–$C_4$-alkyl, CO—$C_1$–$C_4$-alkyl, $SO_2$—O—$C_1$–$C_4$-alkyl or phenyl, by an oxygen or oxygen-containing gas, wherein the oxidation is carried out at 0°–200° C. and 0.2–200 bar in the presence of a catalyst system comprising a palladium compound and one or more reoxidizing agents from the group of compounds of further subgroup metals and quinones, in a microemulsion as reaction medium and catalyst support, wherein the size of the droplets of said microemulsion range from 5 to 100 nm.

2. The process of claim 1, wherein the oxidation is carried out at 0° to 120° C.

3. The process of claim 2, wherein the oxidation is carried out at 10° to 80° C.

4. The process of claim 3, wherein the oxidation is carried out at 15° to 40° C.

5. The process of claim 1, wherein the oxidation is carried out at 0.5 to 100 bar.

6. The process of claim 5, wherein the oxidation is carried out at 1 to 10 bar.

7. The process of claim 1, wherein the microemulsion used is a single-phase system comprising (i) 1–20% by weight of water, (ii) 60–97% by weight of one or more organic components from the group of olefins to be reacted and organic solvents and (iii) 2–20% by weight of one or more surfactants from the group of ionic and nonionic surfactants, where all figures are based on the total weight of the microemulsion.

8. The process of claim 7, wherein the number of surfactants (iii) is 1–3.

9. The process of claim 7, wherein surfactants used are those from the group of n-($C_8$–$C_{18}$)-alkyl-sulphonates, n-($C_8$–$C_{18}$)-alkyl-benzenesulphonates, n-($C_8$–$C_{18}$)-alkyl-trimethyl ammonium salts, di-(n-($C_8$–$C_{18}$)-alkyl-dimethyl-ammonium salts, n-($C_8$–$C_{18}$)-alkyl-carboxylates, oligoethylene oxide ($EO_{2-30}$)-mono-n-($C_6$–$C_{18}$)-alkyl ethers, n-($C_8$–$C_{18}$)-alkyl-dimethylamine oxides, n-($C_8$–$C_{18}$)-alkyl-dimethyl-phosphine oxides or oligoethylene oxide($EO_{2-30}$)-mono-aryl ethers.

10. The process of claim 1, wherein reoxidizing agents used are one or more subgroup metals from the group of iron, cobalt, nickel, copper, chromium, tin, antimony, cerium, rhodium, platinum, gold, preferably iron or copper.

11. The process of claim 10, wherein the catalyst contains $PdCl_2$ or $Pd(NO_3)_2$ and $Fe(NO_3)_3$ or $CuCl_2$.

12. The process of claim 1, wherein the Pd compound of the catalyst makes up 0.0005–10% by weight of the microemulsion and the subgroup metal compounds make up 0.0001–20% by weight of the microemulsion.

13. The process of claim 12, wherein the Pd compound makes up 0.05–1% by weight of the microemulsion and the subgroup metal compound is present in a proportion 2–100 times that of the Pd compound.

14. The process of claim 1, wherein the olefin used has the formula

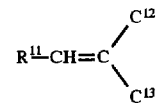

where $R^{11}$ and $R^{12}$ are, independently of one another, hydrogen; straight-chain or branched $C_1$–$C_4$-alkyl which is unsubstituted or substituted by halogen, hydroxy, COO—$CH_3$, CO—$CH_3$ or phenyl; or phenyl which is unsubstituted or substituted by halogen, hydroxy, nitro, $CH_3$, $C_2H_5$, COO—$CH_3$ or CO—$CH_3$, and $R^{13}$ is hydrogen or methyl, and $R^{11}$ and $R^{13}$ or $R^{12}$ and $R^{13}$ can together represent trimethylene, tetramethylene or pentamethylene.

* * * * *